United States Patent [19]

Locke et al.

[11] Patent Number: 5,298,251
[45] Date of Patent: Mar. 29, 1994

[54] FUNGICIDE COMPOSITIONS DERIVED FROM NEEM OIL AND NEEM WAX FRACTIONS

[75] Inventors: James C. Locke, Silver Spring; James F. Walter, Ashton; Hiram G. Larew, III, Hyattsville, all of Md.

[73] Assignee: W. R. Grace & Co.-Conn., New York, N.Y.

[21] Appl. No.: 94,287

[22] Filed: Jul. 21, 1993

Related U.S. Application Data

[63] Continuation of Ser. No. 959,860, Oct. 13, 1992, which is a continuation of Ser. No. 949,180, Sep. 21, 1992, which is a continuation-in-part of Ser. No. 866,968, Apr. 13, 1992, abandoned, which is a continuation of Ser. No. 818,748, Jan. 7, 1992, abandoned, which is a continuation of Ser. No. 637,027, Jan. 3, 1991, abandoned.

[51] Int. Cl.$^5$ .............................................. A01N 25/00
[52] U.S. Cl. .................................... 424/405; 424/410
[58] Field of Search ................. 514/453; 424/405, 410

[56] References Cited

U.S. PATENT DOCUMENTS

| | | | |
|---|---|---|---|
| 4,556,562 | 12/1985 | Larson | 514/453 |
| 5,001,146 | 3/1991 | Carter et al. | 514/453 |
| 5,124,349 | 6/1992 | Carter et al. | 514/453 |

OTHER PUBLICATIONS

"Activity of Neem (Azadirachta Indica A Juss) Seed Kernel Extracts Against the Mustard Aphid, Lipaphis Erysimi," R. P. Singh, C. Devakumar and S. Dhingra, Phytoparasitica, 16(3), 225–230 (1988).

*Primary Examiner*—Thurman K. Page
*Assistant Examiner*—William E. Benston, Jr.
*Attorney, Agent, or Firm*—Beverly K. Johnson

[57] ABSTRACT

Novel fungicide compositions prepared from neem seeds are disclosed. Two distinct neem derived fungicides obtained non-polar, hydrophobic solvent neem seed extracts which are substantially free of azadirachtin, by removing the hydrophobic solvent and cooling the resulting neem oil to separate a semi-solid neem wax fraction and a clarified neem oil fraction.

10 Claims, No Drawings

FUNGICIDE COMPOSITIONS DERIVED FROM NEEM OIL AND NEEM WAX FRACTIONS

This is a continuation of application Ser. No. 959,860, filed Oct. 13, 1992, which is a continuation of application Ser. No. 949,180, filed on Sep. 21, 1992 which is a continuation-in-part of U.S. Ser. No. 866,968, filed Apr. 13, 1991, abandoned which is a continuation of U.S. Ser. No. 818,748, filed Jan. 7, 1992 (abandoned), which is a continuation of U.S. Ser. No. 637,027 filed Jan. 3, 1991 (abandoned).

BACKGROUND OF THE INVENTION

1. Field of the Invention

This invention relates to novel pesticide and fungicide compositions obtained from neem seed extracts prepared by extracting seeds with non-polar hydrophobic solvents. More specifically, a neem wax and a clarified neem oil fraction are prepared which exhibit the consistent ability to repel pests from plant surfaces and to kill pests and fungi at various life stages.

2. Description of Prior Art

The neem tree, a tropical evergreen, has been used for centuries as a source of insecticides to which insects have not developed a resistance. Various neem seed extracts, particularly the ones containing the tetranortriterpenoid azadirachtin, are known to influence the feeding behavior, metamorphosis (insect growth regulating effect), fecundity, and fitness of numerous insect and fungal species belonging to various orders.

Neem seeds also contain an oil substance which has been used for its medicinal and therapeutic properties for centuries. However, "neem oil" has been produced by a number of methods and this has lead to a great variability in the properties of materials designated as "neem oil". Very little chemical characterization has therefore been possible. Many of the publications referring to "neem oil" give no information as to its preparation, which is the key determinant of its composition.

There are two principle methods of removal of oil from neem seeds: expulsion, where the oil is pressed from the seeds, and extraction, where the oil is removed from the seeds by solubilization in a solvent. Inherently, materials made by these methods have very different properties. Oil expelled from the seed will also contain water expelled from the seed by the same process. This aqueous material will carry along with it liminoids, such as azadirachtin, which themselves have insecticidal activity.

Khan et al. (1986) report that neem oil (source unidentified) showed no inhibitory affect on the growth of a variety of fungi. In fact, it is reported that the neem oil was contaminated with molds including *Aspergillus niger* and *Aspergillus flavus*. Similarly, Sharma et al. (1986) report that 3-5% neem seed oils (no method of preparation given) had no effect on the control of pod borer *Heliothis armigera* on chick-pea, and Gujar et al. (1985) report that neem seed oil (no method of preparation given) had no effect on the desert locust, *Schistocerca gregaria*.

Contrary to this, it has been reported that neem oil formulations prepared by expressing oil from the seeds or by extracting with aqueous solvents are effective insecticides and fungicides. It is reported that 10% neem oil (preparation unidentified) (Anon. 1986) inhibited the growth of certain fungi in vitro. Dreyer (1986) discloses that neem oil obtained by hand-pressing in the cold was similar in the control of phytophagous arthropods to aqueous extracts; expeller-pressed oil was much less active. Singh et al. (1980) reports that neem oil obtained with a Soxhlet apparatus, no solvent given, controls fungi including *Fusarium oxysporum, Rhizoctonia solani, Sclerotium rolfsii* and *Sclerotia sclerotiorum*. It is likely that all of these materials contained appreciable polar moieties, including several liminoids.

Similarly, neem oil has been reported to have insecticidal properties but the reports of efficacy are often in conflict, perhaps because of significant differences in the composition of the "neem oil" tested. Furinstau et al. (1985) report that a 1% suspension of neem oil (no method of preparation identified) is effective at controlling aphids but is phytotoxic to sorghum plants. Yet Saxena et al. (1984) report that a >6% suspension of neem oil is necessary to achieve statistical control of the plant hopper *Nilaparatu lugens* on rice seedlings, apparently with no phytotoxic effect.

Hydrophobic solvent extracted neem oil is disclosed in U.S. Ser. No. 07/456,762 (Locke et al.). It is taught that the disclosed formulations exhibit the ability to repel insects from plant surfaces, prevent fungal growth and kill insect and fungal pests at various life stages.

It has now been discovered that consistent fungicidal and insecticidal neem fractions can be obtained from hydrophobic solvent extracted neem oil by fractionating the neem oil by cooling to obtain a neem wax fraction and a clarified neem oil fraction. Furthermore, it is shown that freeze fractionation of the neem oil produces a lower-phytotoxic clarified neem oil material.

SUMMARY OF THE INVENTION

In accordance with the present invention, there are provided certain novel insecticidal and fungicidal formulations derived from non-polar, hydrophobic solvent neem oil extracts which are substantially free of azadirachtin, and which, following removal of the solvent to yield neem oil, are further separated into distinct fractions: a clarified neem oil fraction and a neem wax fraction. These fractions exhibit the ability to repel and kill pest, i.e., insect larvae as well as adults, and control foliar and surface fungal pathogens.

U.S. Ser. No. 07/456,762 (Locke et al.) teaches that non-polar hydrophobic solvent extracts of ground neem seed yield a neem oil product that can have combined insecticidal and fungicidal activities. The present invention teaches improvement of the neem oil product by fractionating to separate the waxes from the oils. The clarified neem oil demonstrates increased insect repellency, decreased phytotoxicity, decreased skin irritability, increased fungicidal activity and increased wetting ability. The neem wax demonstrates increased insect repellency, increased fungicidal activity and increased wetting ability.

It is therefore an object of this invention to provide novel natural insecticides derived from the clarified neem oil fraction or neem wax fraction of non-polar solvent-extracted neem oil. It is further intended that these novel insecticides will repel and kill insects pests at various life stages.

It is also an object of this invention to provide novel natural fungicides which will kill and control various pathogenic fungi.

An additional object is to provide novel natural insecticides and fungicides which repel and kill insects and pathogenic fungi on plant surfaces. Related objects are to provide methods of preparing and using the novel natural insecticides.

Another object of this invention is to provide natural insecticide formulations derived from neem seeds for protecting stored fruit and grains from various insecticides or fungal pests.

A further object of this invention is to provide natural insecticide formulations derived from neem seeds that can protect animals from various pests or fungi.

It is also an object of this invention to provide natural insecticide formulations derived from neem seeds that can protect stored objects such as books, papers or cloth from various pests or fungi.

A final object of the invention is to provide novel neem-based insecticide and fungicide compositions having one or more of the following characteristics: insect repellency, low phytotoxicity, low skin irritation, and good wetting ability.

DETAILED DESCRIPTION

As used herein, the term "insecticide" or "insecticidal" is intended to encompass insect repellents, insecticides, larvacides, ovicides and the like. The term "insecticidally effective amount" or "fungicidally effective amount" means that dosage of active substance sufficient to exert the desired insecticidal or fungicidal activity. The terms "clarified neem oil" or "neem oil fraction" are used herein interchangeably to designate a non-polar hydrophobic solvent extracted neem oil which has been fractionated by cooling to about 5° C. to 15° C. to precipitate therefrom solidified neem wax fractions. The term "neem wax" or neem wax fraction" is used herein interchangeably to designate a semi-solid neem wax fraction precipitated from a non-polar hydrophobic solvent extracted neem oil by cooling the oil to about 5° C, to about 15° C. The term "neem fractions" is used herein to designate the clarified neem oil and the neem wax fraction. The term "crude neem oil" is used herein to designate a non-polar hydrophobic solvent extracted neem oil obtained by removal of the nonpolar solvent.

Some active ingredients of the seeds and leaves of the tropical neem tree, *Azadirachtin indica,* particularly the tetranortriterpenoid azadirachtin, are known for their potent insecticidal activities. The present invention is directed to clarified neem oil and neem wax fractions that are substantially free of azadirachtin and yet possess the ability to repel insect pests from surfaces, kill and repel insect pests at various life stages and prevent fungal growth on plant and other surfaces. For purposes of the present invention, the term "substantially free of azadirachtin" is used herein to indicate clarified neem oil and neem wax fractions having less than 1.0 weight percent, preferably less than 0.3 weight percent, most preferably less than 0.03 weight percent, of azadirachtin.

The insecticides and fungicides of this invention are prepared from neem oil extract obtained by extracting neem seeds or expressed neem oil with a suitable non-polar, hydrophobic solvent. Preferably, neem seeds are coarsely ground for extraction of the neem oil. It will also be possible to treat neem oil that has been physically expressed from the seeds by commonly practiced methods. However, treatment of expressed oil to form the neem fractions of this invention is less preferred than direct solvent extraction from neem seeds.

Suitable non-polar hydrophobic solvents for use in extracting the neem oil from the neem seeds or expressed neem oil will include those non-polar hydrophobic solvents having high neem oil solubility and substantially no azadirachtin solubility. The preferred non-polar hydrophobic solvents include, but are not limited to, aliphatic hydrocarbons such as pentane, hexane, heptane, octane, nonane, decane, isooctane, cyclohexane, and isomers thereof; petroleum distillates, petroleum ether, and the like; aromatics such as benzene, toluene, and the like; substituted aromatics such as chlorobenzene, benzaldehyde, xylenes, and the like; and mixtures thereof. Various other non-polar hydrophobic solvents having the above characteristics are well known to those skilled in the art, and the choice of a particular solvent is not critical to the invention, provided that the solvent is non-polar, hydrophobic, and exhibits little azadirachtin solubility and a high degree of neem oil solubility.

The solvent is then stripped from the neem oil extract at the lowest practical temperature to prevent degradation, preferably being removed by vacuum evaporation, although other methods may be used. The resulting neem oil is then fractionated. Hydrophillic and hydrophobic solvents may be used to fractionate the neem oil. For example, co-solvents such as ethanol and hexanol can facilitate fractionation of the oil. The oil is cooled to about 5° to 15° C., preferably less than about 10° C., whereupon certain waxes and fatty acids contained therein solidify. The solid components are filtered out to obtain a semi-solid neem wax fraction. The remaining liquid filtrate is retained as clarified neem oil of the crude neem oil.

The 5°–15° C. temperature range represents the transition temperature range of the neem wax fraction between its clear liquid form and its yellow white solid form. The fraction that clouds the oil and then precipitates out is the neem wax fraction. The remaining clarified oil fraction, on the other hand, remains a clear liquid down to 5° C.

The two fractions possess distinct insecticidal, fungicidal and phytotoxic properties. While both the clarified neem oil and neem wax fractions of the invention exhibit useful insecticidal and fungicidal properties, consequently, it has been discovered that there are certain applications where it may be advantageous to use either the oil or wax fraction.

The clarified neem oil, which is an orange brown liquid at room temperature, has very low phytotoxicity and causes little or no irritation on contact with plant surfaces. It exhibits the ability to kill not only insect larvae, but also insects in the egg and adult stage. Application at the egg stage causes large numbers of the eggs to shrivel, eliminating hatching. Where hatching occurs, many nymphs die upon emergence from the egg case. Treatment of plants also acts to repel adult insects, preventing eggs from being deposited. In addition, this neem oil fraction is a potent foliar and skin fungicide.

Clarified neem oil can be effectively used as a spray on surfaces to control various pests and fungi on a variety of plants, stored grains, and animals. Furthermore, it can be used to protect stored books, rugs, or other materials normally attacked by pests, i.e., insects, and fungi by adding as an aerosol spray or mist or by incorporation into the manufacturing process. Finally, it can be applied as a soap, gel, liquid, salve, or the like, to repel insects and protect skin or wool from insect and fungal attack.

In comparison, neem wax is a yellow-white, flowable semi-solid at room temperature (melting point about 5°–15° C., preferably about 10° C.). It has the same general insecticidal and fungicidal effects as the neem oil fraction. It exhibits a superior ability to kill insect eggs. However, it may not be quite as effective as clarified neem oil for foliar uses, as it exhibits a higher phytotoxicity than clarified neem oil. Formulations containing neem wax may be particularly suitable for use as a dormant spray prior to the emergence of foliage on the plant.

The neem wax fraction may be used as a protectant for paper or textiles, i.e. for books and woolen fabrics. Due to the semi-solid state of the neem wax fraction at room temperature, the treated surface would feel dry rather than oily. In addition, it can easily be incorporated in protective soaps, repellent sticks and repellent candles.

The neem formulations or fractions of this invention are effective to control such insect pests as Colorado Potato Beetle, Diamond Backed Moth, Whitefly, Mealy bug, Aphids, Hornworm, Lacebug, mites, fleas, ticks, mosquitoes and flies and the like. They are also effective at controlling fungi such as mildews, rusts, dollar spot, brown patch, black spots, botrytis, and the like. Furthermore, the neem oil can be used to control parasitic pests on mannals such as lice, ticks, scabies, as well as eczema and dermatitus. The neem formulations of this invention are particularly useful to repel moths in a confined space, i.e., closets.

In the compositions and formulations of the invention, the clarified neem oil or neem wax fraction may be used alone or mixed with conventional inert agronomically or physiologically acceptable (i.e. plant and mammal compatible and/or insecticidally inert) diluents or extenders usable in conventional compositions or formulations as is well known in the art. If desired, adjuvants such as surfactants, stabilizers, antifoam agents and antidrift agents may also be added. Examples of compositions and formulations according to the invention include aqueous or other agronomically acceptable suspensions and dispersions, oily dispersions, pastes, dusting powders, wettable powders, emulsifiable concentrates, flowables, granules, baits., invert emulsions, aerosol compositions and fumigating candles.

The compositions and formulations are prepared in a known manner to one skilled in the art, for example by extending the active compounds with conventional dispersible liquid diluent carriers and/or dispersible solid carriers optionally with the use of carrier vehicle assistants, e.g., conventional surface-active agents, including emulsifying agents and/or dispersing agents, whereby, for example, in the case where water is used as diluent, organic solvents may be added as auxiliary solvents.

Adhesives such as carboxymethylcellulose and natural and synthetic polymers in the form of powders, granules or lattices, such as gum arabic, polyvinyl alcohol, polyvinyl cellulose, and polyvinyl acetate, can be used in the formulations to improve the adherence of this insecticide. Furthermore, a lubricant such as calcium stearate or magnesium stearate may be added to a wettable powder or to a mixture to be granulated.

In general, insecticide and fungicide formulations in accordance with this invention can be prepared by diluting the clarified neem oil or neem wax fraction with about 0.1 to 50% by volume surfactant, inert ingredient or diluent. The formulation may then be further diluted with water to form a 0.1 to 10%, preferably 0.1 to 5%, suspension before application. These dilutions are intended to provide usable ranges for both the wax and clarified oil fractions, with the understanding that the fractions will be diluted to the desired and appropriate fluidity for the intended purpose (i.e., as an insecticide and/or fungicide for one or more applications).

One or more surfactants may typically be used in preparing the insecticide formulations. Non-ionic surfactants will generally be preferred. Examples include, but are not limited to, Triton B-1956, Tween-20, sodium dodecylsulfide and the like. For certain applications, anionic surfactants (such as Ivory ® liquid soap or the like) may be preferred. Where aqueous diluents or ingredients are used, an emulsifying surfactant should be used. Selection of surfactants, inert ingredients and diluents will depend on the application and are well known to those of ordinary skill in the art.

The clarified neem oil or neem wax fractions of the present invention may be employed alone and/or with such solid and/or liquid dispersible carrier vehicles and/or with other known compatible active agents, especially plant protection agents, such as other insecticides, arthropodicides, nematicides, fungicides, bactericides, rodenticides, herbicides, fertilizers, growth-regulating agents, synergists, etc., if desired, or in the form of particular dosage preparations for specific applications made therefrom, such as emulsions, suspensions, powders, pastes, and granules which are thus ready for use. It may also be desired to mix one (or both) of the neem fractions of this invention with one or more active ingredients. For example, useful but environmentally toxic or phytotoxic chemical insecticides can be used at a reduced, and thereby safer, level by use as a co-insecticide with the products of this invention. Also, it may be desired to add a neem wax component to a standard insecticide and/or fungicide formulation to make the material more resistant to being washed off.

The following examples are provided to illustrate the invention in accordance with the principles of this invention, but are not to be construed as limiting the invention in any way except as indicated in the appended claims.

EXAMPLE 1

This example illustrates the effectiveness of the clarified neem oil and neem wax fractions of this invention on newly laid or near-to-hatch greenhouse whitefly (*Trialeurodes vaporariorum*) eggs. These fractions were obtained by first extracting 180 lb. neem seed with 150 gal. hexane in an agitated vessel at room temperature for 20 hours. The seeds were then separated from the hexane-oil extract by centrifugation and the hexane-oil extract was evaporated at 60° C. until 35 lbs. of a thick brown neem oil product was obtained. The neem oil product was cooled to 10° C. and then filtered to remove precipitated waxes. Thirty pounds of clarified neem oil containing 0.02 weight percent of azadirachtin were obtained along with 5 lbs. of neem wax.

The clarified neem oil fraction and neem wax fraction each were formulated into 1% and 3% solutions in 100 ml water containing one drop of surfactant (Ivory TM liquid soap). To test the effectiveness of the formulations, 50 potted chrysanthemum plants cv. Iceberg had all but 3 fully-expanded leaves removed. The plants were placed in a whitefly colony for 24 hours, removed, and sprayed with a water-mist to remove the adult whiteflies from the plants. The plants were divided into ten groups of five plants and treated as follows:

Group 1: sprayed with water 0 days after exposure (DAE) to whiteflies,
Group 2: sprayed with 1% clarified neem oil formulation 0 DAE,
Group 3: sprayed with 3% clarified neem oil formulation 0 DAE,
Group 4: sprayed with 1% clarified neem oil formulation 4 DAE,
Group 5: sprayed with 3% clarified neem oil formulation 4 DAE,
Group 6: sprayed with water 0 days after exposure (DAE) to whiteflies,
Group 7: sprayed with 1% neem wax formulation 0 DAE,
Group 8: sprayed with 3% neem wax formulation 0 DAE,
Group 9: sprayed with 1% neem wax formulation 4 DAE, and
Group 10: sprayed with 3% neem wax formulation 4 DAE.

Greenhouse whitefly eggs usually hatch 5-6 days after oviposition, thus the 4 DAE treatments (Groups 4 and 5) were applied near the time of egg hatch. Once all the eggs had hatched on the control plants (Groups 1 and 6, those sprayed with water), the effectiveness of each neem formulation was assessed by counting the eggs and dead nymphs per leaf. The results were as follows:

TABLE 1

Effect of Clarified Neem Oil or Neem Wax Formulations When Sprayed on New and 4-Day Old Greenhouse Whitefly Eggs Laid on Chrysanthemums

| Trial | Treatment | Eggs[1] | Dead Nymphs[2] | % Mortality[3] |
|---|---|---|---|---|
| Clarified Oil: | | | | |
| Group 1 | Water | 180 a | 27 b | 15 |
| Group 2 | 1%, 0 DAE | 126 a | 118 a | 94 |
| Group 3 | 3%, 0 DAE | 137 a | 131 a | 96 |
| Group 4 | 1%, 4 DAE | 173 a | 121 a | 70 |
| Group 5 | 3%, 4 DAE | 130 a | 124 a | 95 |
| Wax: | | | | |
| Group 6 | Water | 314 bc | 3 d | 0 |
| Group 7 | 1%, 0 DAE | 401 ab | 310 b | 77 |
| Group 8 | 3%, 0 DAE | 198 c | 197 c | 99[4] |
| Group 9 | 1%, 4 DAE | 311 bc | 303 b | 97[4] |
| Group 10 | 3%, 4 DAE | 511 a | 511 a | 100[4] |

[1]Values are means per 100 cm$^2$ leaf area. Means within trial followed by the same letter are not significantly different; DMRT, P = 0.05, N = 15 leaves.
[2]"Dead Nymphs" include shrivelled eggs (in which the nymph did not emerge but was nevertheless dead).
[3]Number of dead nymphs divided by the number of eggs.
[4]Most eggs shrivelled.

The clarified neem oil and neem wax fractions at both concentrations and exposure times caused significant nymphal mortality. The clarified neem oil fraction caused slightly less mortality when applied as a 1% spray to older eggs than at other strengths and times. The neem wax fraction caused most of the eggs to appear shriveled with the 3% spray at both treatment times, and with the 1% spray at 4 DAE. Mortality was primarily observed at the egg or newly hatched nymphal stage. It appears that while clarified neem oil is particularly effective in killing whitefly nymph, the neem wax is particularly effective in killing whitefly eggs.

EXAMPLE 2

This example illustrates the effectiveness of the clarified neem oil fraction and the neem wax fraction as repellents against adult *Bemisia tabaci* whiteflies when sprayed on chrysanthemum foliage. Clarified neem oil and neem wax formulations were prepared according to Example 1. To test the effectiveness of the formulations, eighteen 3-week-old potted chrysanthemum plants cv. Iceberg, having all but 3 fully expanded leaves removed, were divided into six groups of three and treated as follows:
Group 1: sprayed with water,
Group 2: sprayed with 1% clarified neem oil formulation,
Group 3: sprayed with 3% clarified neem oil formulation,
Group 4: sprayed with water,
Group 5: sprayed with 1% neem wax formulation,
Group 6: sprayed with 3% neem wax formulation,
and then exposed to a colony of whiteflies for 24 hours. After exposure, the plants were cleaned of whiteflies and the number of eggs per leaf was determined. The results were as follows:

TABLE 2

Effectiveness of Clarified Neem Oil and Neem Wax Formulations as Repellents Against *Bemisia tabaci* on Chrysanthemums

| Trial | Treatment | Eggs[1] |
|---|---|---|
| Clarified Oil: | | |
| Group 1 | Water | 33.1 a |
| Group 2 | 1% | 1.4 b |
| Group 3 | 3% | 1.3 b |
| Wax: | | |
| Group 4 | Water | 63.6 a |
| Group 5 | 1% | 7.2 b |
| Group 6 | 3% | 0.2 b |

[1]Values are means calculated per 100 cm$^2$ leaf area. Means in the same trial followed by the same letter are not significantly different; DMRT, P = 0.05, N = 9 leaves.

The results show that all the clarified neem oil and neem wax formulations were effective at repelling whiteflies.

EXAMPLE 3

This example illustrates the longevity of repellant action of both the neem wax and clarified neem oil fractions when sprayed on chrysanthemum cv. Iceberg foliage. Repellency was quantified by counting the number of greenhouse whitefly (*Trialeurodas vaporariorum*) eggs laid on leaves. Clarified neem oil and neem wax formulations were prepared according to Example 1 Forty eight 3-4 week old chrysanthemum plants cv. Iceberg having all but 3 fully expanded leaves removed, were divided into three groups of 16 plants each and treated as follows:
Group 1: sprayed with water,
Group 2: sprayed with 1% clarified neem oil formulation,
Group 3: sprayed with 3% clarified neem oil formulation,
Group 4: sprayed with water,
Group 5: sprayed with 1% neem wax formulation,
Group 6: sprayed with 3% neem wax formulation.

On the same day as spraying (Day 0) four plants from each group were placed in a whitefly colony for 24 hours. On days 3, 7 and 14, four more plants from each group were exposed to the whitefly colony for 24 hours. After each exposure, the number of eggs per 100 cm$^2$ of leaf area on the top two leaves were counted. The results were as follows:

TABLE 3

Clarified Neem Oil and Neem Wax -- Residual Effects

| Test | Treatment | Mean No. Eggs[1] | | | |
|---|---|---|---|---|---|
| | | Day 0 | Day 3 | Day 7 | Day 14 |
| Clarified Oil: | | | | | |
| Group 1 | Water | 434 a | 376 a | 640 a | 514 a |
| Group 2 | 1% | 34 b | 47 b | 82 b | 75 b |
| Group 3 | 3% | 13 b | 10 b | 37 b | 46 b |
| Wax: | | | | | |
| Group 4 | Water | 522 a | 470 a | 404 a | 431 a |
| Group 5 | 1% | 55 b | 89 b | 46 b | 67 b |
| Group 6 | 3% | 7 b | 3 b | 6 b | 1 b |

[1]Values are means per 100 cm$^2$ leaf area. Means within trial followed by the same letter are not significantly different; DMRT, P = 0.05, N = 8 leaves.

Both the clarified neem oil and the neem wax formulations effectively repelled ovipositing *T. vaporariorum* for up to 14 days after spraying. There were no clear differences in the level of repellence between the need oil and need wax fractions, nor between the two concentrations tested. Although not statistically different from 1% concentration, generally the 3% clarified neem oil and neem wax formulations reduced the number of eggs laid to lower levels. The neem wax formulations appeared to have somewhat greater longevity of repellency over the 14 days of this test.

EXAMPLE 4

This example illustrates the effectiveness of neem oil, clarified neem oil, and neem wax on bean rust control. Clarified neem oil and neem wax fractions were prepared according to Example 1. Neem oil product was prepared according to Example 1, stopping after the hexane was evaporated from the neem oil extract to yield the neem oil product. One percent solutions of neem oil product, clarified neem oil, and neem wax were prepared in water and sprayed on bean leaves. These leaves were then inoculated with bean rust spores, placed in a dew chamber for 16 hours and then moved to the greenhouse. After seven days, the number of rust pustules per leaf area were counted. The results, presented in Table 4, show that the clarified neem oil formulation showed the greatest reduction in pustules present. The neem wax formulation had the lowest reduction, although it exhibited a statistically significant improvement over the control.

TABLE 4

| Treatment | Pustules[1] | % Control |
|---|---|---|
| Control | 5,900 a | 0 |
| 1% Neem Wax | 1,302 b | 78 |
| 1% Neem Oil Product | 840 bc | 86.1 |
| 1% Clarified Neem Oil | 573 c | 90.3 |

[1]Values are means calculated per 100 cm$^2$ leaf area. Means in the same trial followed by the same letter are not significantly different; DMRT, P = 0.05, N = 9.

EXAMPLE 5

This example illustrates the effectiveness of the clarified neem oil and neem wax fractions of this invention against the whitefly. It also illustrates lack of phytotoxicity of the neem oil fraction on tomato and Pelargonum seedlings with repeated applications.

TABLE 5

| Trial | Treatment | Whitefly Count[1] | |
|---|---|---|---|
| | | Tomato | Pelargonum |
| 1 | Water | 4 | 3.25 |
| 2 | 1:100 Clarified Neem Oil | 3 | 2.0 |
| 3 | 1:50 Clarified Neem Oil | 1.5 | 1.25 |
| 4 | 1:100 Neem Wax | — | — |
| 5 | 1:50 Neem Wax | — | — |

[1]Scale for whitefly count at 9 weeks:
1 = 0 whitefly scales/larvae
2 = less than 10
3 = 10 to 50
4 = greater than 50

The plants were sprayed weekly. The greenhouse whitefly population was at a low level. Plants in Treatment 1 (Control) showed significantly higher numbers of adult whiteflies than any of the neem treatments after 5 weeks.

After 6 weeks, Treatments 4 and 5 demonstrated extensive, phytotoxicity (leaf injury) on both plant types. Applications of Treatments 4 and 5 were discontinued and plants in these treatments discarded.

After 9 weeks, Treatments 2 and 3 continued to exhibit no phytotoxicity on either plant type. Whitefly counts were made.

EXAMPLE 6

This example demonstrates the effectiveness of clarified neem oil formulations for protection against powdery mildew development on greenhouse hydrangeas. Clarified neem oil was prepared according to Example 1. A 1% dilution of clarified neem oil was sprayed onto hydrangeas every 14 days. Comparison was made to a first control in which the plants were sprayed with water and a second control in which plants were sprayed with Sunspray TM insecticide, a commercially available formulation. Five plants were used in each test group. Each plant was examined for the presence of mildew on its leaves. The results, shown in Table 6, demonstrate that the clarified neem oil formulation is effective in preventing development of powdery mildew.

TABLE 6

Effect of Clarified Neem Oil Spray on Powdery Mildew Development

| Test | Treatment | Mildew[1] + | Mildew[1] − | % Leaves Mildew + |
|---|---|---|---|---|
| Group 1 | Water | 48.6 | 57.0 | 46.0% |
| Group 2 | 1% Clarified Neem Oil | 1.8 | 101.4 | 1.7% |
| Group 3 | 1% Sunspray Insecticide | 0.2 | 92.0 | 0.2% |

[1]Counts represent average number of leaves with mildew present (+) or absent (−).

EXAMPLE 7

This example demonstrates the decreased phytotoxicity of clarified neem oil as to compared to crude neem oil and neem wax.

Neem oil obtained by extruding Neem seeds with hexane and evaporation of this hexane was clarified by cooling to 5° C. and filtering off the resulting wax. Each of the three materials, crude Neem oil, clarified Neem oil and Neem wax was then formulated with 10% surfactant B-1956 sold by Rohm and Haas of Philadelphia, Pa., and then diluted in water at a rate of 1%. This solution was then sprayed on Hybred Red Elite Geranium flowers each week for a period of three weeks.

The day after each spray, the damage to the flowers was measured as outlined in Table 7.

TABLE 7

PHYTOTOXICITY OF NEEM FRACTION ON RED ELITE HYBRED GERANIUM

| | |
|---|---|
| Crude Oil | 3.6 |
| Neem Wax | 3.5 |
| Clarified Oil | 1.2 |

Key: 1 = None, 2 = Slight, 3 = Moderate, 4 = Severe

Without further elaboration, it is believed that one skilled in the art, using the preceding detailed description and examples can utilize the present invention to its fullest extent. The principles, preferred embodiments and modes of operation of the present invention have been described in the foregoing specification. Variations and changes may be made by those skilled in the art without departing from the spirit of the invention. All parts and percentages are by weight unless otherwise indicated.

What is claimed is:

1. A method of preparing fungicides derived from neem seeds or expressed neem oil, which fungicides are substantially free of azadirachtin, comprising
    (a) extracting neem seeds with a non-polar, hydrophobic solvent to obtain a need oil extract;
    (b) removing the solvent from the neem oil extract to obtain a neem oil;
    (c) cooling the neem oil to a temperature sufficient to partially solidify and precipitate a neem wax having fungicidal activity;
    (d) separating and recovering the neem wax from the neem oil to obtain a clarified neem oil having fungicidal activity; and
    (e) recovering the clarified neem oil.

2. The method of claim 1 in which the neem oil is cooled to about 5° C. to about 15° C.

3. A fungicidal neem wax produced by the method of claim 1.

4. A fungicidal clarified neem oil produced by the method of claim 1.

5. A method for controlling fungi comprising applying to a surface to be protected an effective fungicidal amount of one or more neem seed derived fungicides which are substantially free of azadirachtin and which are prepared by:
    (a) extracting neem oil from neem seeds or expressed neem oil with a non-polar, hydrophobic solvent to obtain a neem oil extract;
    (b) removing the solvent from the neem oil extract to obtain neem oil;
    (c) cooling the neem oil to a temperature sufficient to partially solidify a neem wax having fungicidal activity;
    (d) separating the recovering the neem wax fungicide from the neem oil extract; and
    (e) recovering a clarified neem oil having fungicidal activity.

6. The method of claim 5 in which the surface to be protected is fruits, grains or vegetables.

7. The method of claim 5 in which the surface to be protected is selected from the skin, fur or wool of mammals.

8. The method of claim 5 in this the fungicides are applied in a carrier or adjuvant suitable for human application.

9. The method of claim 5 in which the surface to be protected is selected from paper, textile or plant.

10. The method of claim 5 in which the fungi is selected from mildews, rusts, dollar spots, brown patch, black spots and botrytis.

* * * * *